US00PP22196P3

(12) United States Plant Patent
Franke

(10) Patent No.: US PP22,196 P3
(45) Date of Patent: Oct. 11, 2011

(54) ***DIANELLA TASMANICA* PLANT NAMES 'TAS300'**

(50) Latin Name: *Dianella tasmanica*
Varietal Denomination: TAS300

(76) Inventor: Kahn Franke, Smith's Gully (AU)

( * ) Notice: Subject to any disclaimer, the term of this patent is extended or adjusted under 35 U.S.C. 154(b) by 0 days.

(21) Appl. No.: 12/378,348

(22) Filed: Feb. 13, 2010

(65) Prior Publication Data

US 2010/0293687 P1 Nov. 18, 2010

Related U.S. Application Data

(60) Provisional application No. 61/065,853, filed on Feb. 15, 2008.

(51) Int. Cl.
*A01H 5/00* (2006.01)

(52) U.S. Cl. ..... Plt./424

(58) Field of Classification Search ..... Plt./424
See application file for complete search history.

*Primary Examiner* — June Hwu
*Assistant Examiner* — Louanne Krawczewicz Myers

(57) ABSTRACT

'TAS300' is a distinctive variety of *Dianella tasmanica,* which is characterized by its combination of presence of leaf variegation, medium-tall plant height, broad leaf blade and stability and uniformity of traits through successive cycles of asexual propagation.

1 Drawing Sheet

Latin name of the genus and species: The Latin name of the novel variety disclosed herein is *Dianella tasmanica* 'TAS300'.

Variety denomination: The inventive variety of *Dianella tasmanica* disclosed herein has been given the variety denomination 'TAS300'.

BACKGROUND OF THE INVENTION

The present invention relates to a new and distinct variety of evergreen perennial *Dianella tasmanica,* which has been named 'TAS300'. *Dianella* are a genus of ornamental grass-like plants. In general, *Dianella tasmanica* has flax-like leaves.

An application for plant breeders' rights for 'TAS300' has been lodged with the Australian Plant Breeders Rights Office, and was received on 16 Mar. 2007 (under Application No. 2007/097).

Parentage: The cultivar 'TAS300' was discovered in 1998 at a nursery in Smiths Gully, Victoria, Australia, during a seedling selection of open pollinated, unnamed *Dianella tasmanica* (unpatented). The parent is characterized by an absence of leaf variegation. Selection criteria for 'TAS300' was presence of leaf variegation.

Asexual reproduction. The new variety 'TAS300' was first asexually propagated by vegetative division in the state of Victoria, Australia in 1999 and has been asexually propagated since that time by division and micropropagation. The distinctive characteristics of cultivar 'TAS300' have remained stable and true to type through successive cycles of asexual propagation.

SUMMARY OF THE INVENTION

'TAS300' is a distinctive variety of *Dianella tasmanica,* which is characterized by its combination of presence of leaf variegation, medium-tall plant height, broad leaf blade and stability and uniformity of traits through successive cycles of asexual propagation.

BRIEF DESCRIPTION OF THE DRAWINGS

The FIGURE shows a *Dianella tasmanica* 'TAS300' plant at approximately 15-months of age. The plant was propagated in a greenhouse and was transferred to the field at six months and grown out in full sun for the final nine months.

DETAILED BOTANICAL DESCRIPTION OF THE VARIETY

The following is a detailed botanical description of a new and distinct variety of *Dianella tasmanica* known as 'TAS300' based upon observations of 15-month old plants grown in nursery pots in full sun in open beds in Clarendon, New South Wales, Australia during autumn 2007-spring 2007. Plant observations and descriptions were taken in spring 2007.

Those skilled in the art will appreciate that certain characteristics will vary with older or, conversely, with younger plants. 'TAS300' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 1995 edition.

'TAS300' is an evergreen perennial *Dianella tasmanica.* 'TAS300' is a semi-erect plant with broad variegated leaf blades, weak leaf arching, green and pale yellow leaf color.

A botanical description of 'TAS300' and comparisons with other varieties of *Dianella tasmanica* are provided below.

Technical Description of the Variety.

Plant characteristics: Growth habit semi-erect, height medium-tall (mean foliar height in a 200 mm pot 36 cm), medium width (mean width 80 cm ) shoot density sparse to medium, stem internode length very short. Internode length varies according to growth rate. Typical interode is 1-2 mm;

Leaves: Attitude semi-erect, leaves clasp, very short stem (approximately 1-2 mm), length long (800 mm), width broad (mean 25 mm), arching is weak, leaf arrangement is alternate, leaf venation is parallel and linear along blade, leaf venation colors visible on leaf 2, primary venation color on upper side green (RHS 137A), secondary venation color on upper side cream (RHS 160D), primary venation color on lower side greyed green (RHS191A) and secondary venation color on lower side cream (160D). Variegation present and striped parallel to vein, degree of variegation is approximately 20-30% of leaf area, glaucosity of upper side medium to strong, upper side color (waxiness removed) corresponds to yellow green (RHS 147A) with secondary color yellow (RHS 12D), primary lower side color (waxiness removed) corresponds to greyed green (RHS 191A), shape linear, apex acute, cross section concave, margin with spines present with weak to medium prominence, midrib lower side with spines present with weak to medium prominence.

Basal sheath: Anthocyanin coloration (summer) red-purple (RHS 53B) with a strong intensity.

Basal shoots: Attitude semi-erect, arrangement cluster.

Flowers/Fruit: 'TAS300' has not been observed or flower or produce fruit of berries to date.

Cold and heat tolerance: 'TAS300' has cold and heat tolerance typical of *Dianella tasmanica.*

Drought tolerance: 'TAS300' has drought tolerance typical of *Dianella tasmanica.*

Pest resistance: No known insect pests. 'TAS300' has disease tolerance typical of *Dianella tasmanica.*

Cultural conditions: 'TAS300' can tolerate low nutrient conditions; it does not like continually wet soil conditions, but can tolerate well-draining sandy soils to very heavy clay soils. pH characteristics of the variety are fairly adaptable.

Comparisons with other *Dianella:*

'TAS300' is a more attractive ornamental plant as compared with the parent. 'TAS300' is characterized by a variegated yellow green leaf blade color with contrasting pale yellow as compared with the parent *D. tasmanica* which has no variegation of the leaf blade.

*Dianella* 'TAS 100' (U.S. Plant Pat. No. 19,338) is the most similar comparator variety to 'TAS300'. In comparison with 'TAS100', cultivar 'TAS300' has a medium-tall plant height (approximately 36 cm) whereas 'TAS100' has a short-medium plant height (approximately 25 cm). 'TAS300' has weaker leaf arching than 'TAS100'. 'TAS300' has a degree of variegation of approximately 20-30% of leaf area whereas 'TAS100' has a larger degree of variegation of approximately 30-40%.

'TAS300' can also be compared to the varieties *D. tasmanica* 'Splice' (unpatented) and *D. tasmanica* 'Rainbow' (unpatented). 'TAS300' has medium to strong glaucosity of the leaf blade upper side whereas 'Splice' and 'Rainbow' have very weak leaf blade glaucosity. Anthocyanin coloration is absent in the leaf blade of 'TAS300' whereas it is present and strongly conspicuous in 'Rainbow' and present and mildly conspicuous in 'Splice'. 'TAS300' has a semi-erect leaf attitude whereas 'Splice' has a semi-erect to erect leaf attitude and 'Rainbow' has a more erect leaf attitude.

That which is claimed is:

1. A new and distinct variety of *Dianella tasmanica* plant named 'TAS300', substantially as described and illustrated herein.

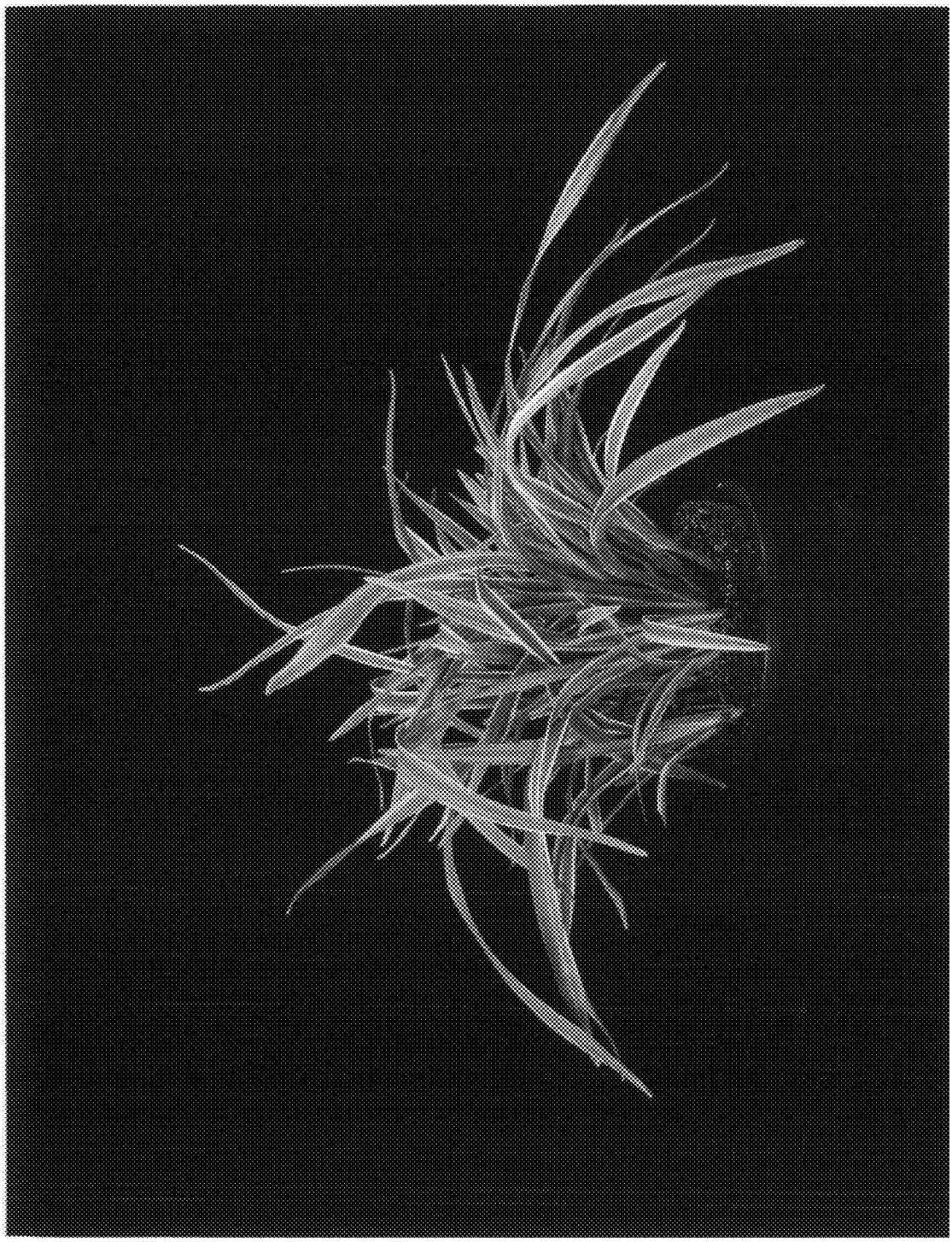

* * * * *